(12) United States Patent
D'Este et al.

(10) Patent No.: US 9,034,624 B2
(45) Date of Patent: May 19, 2015

(54) PROCESS FOR THE SYNTHESIS OF CONJUGATES OF GLYCOSAMINOGLYCANES (GAG) WITH BIOLOGICALLY ACTIVE MOLECULES, POLYMERIC CONJUGATES AND RELATIVE USES THEREOF

(75) Inventors: Matteo D'Este, Abano Terme (IT); Davide Renier, Abano Terme (IT); Gianfranco Pasut, Abano Terme (IT); Antonio Rosato, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 397 days.

(21) Appl. No.: 13/378,660

(22) PCT Filed: Jun. 4, 2010

(86) PCT No.: PCT/EP2010/003634
§ 371 (c)(1),
(2), (4) Date: Jan. 26, 2012

(87) PCT Pub. No.: WO2010/145821
PCT Pub. Date: Dec. 23, 2010

(65) Prior Publication Data
US 2012/0114602 A1 May 10, 2012

(30) Foreign Application Priority Data
Jun. 16, 2009 (IT) .............................. MI2009A1065

(51) Int. Cl.
*C08B 37/08* (2006.01)
*A61K 31/726* (2006.01)
*C08B 37/00* (2006.01)

(52) U.S. Cl.
CPC ............ *C08B 37/0072* (2013.01); *A61K 31/726* (2013.01); *C08B 37/0063* (2013.01); *C08B 37/0069* (2013.01); *C08B 37/0075* (2013.01)

(58) Field of Classification Search
USPC .......... 435/6, 91.1, 455, 458, 188, 6.1; 514/1, 514/2, 44, 53; 536/123.13, 23.1; 530/395, 530/399; 548/546; 424/1.53, 179.1, 85.4
See application file for complete search history.

(56) References Cited

U.S. PATENT DOCUMENTS

| 4,582,865 A | 4/1986 | Balazs et al. |
| 4,636,524 A | 1/1987 | Balazs et al. |
| 6,153,655 A | 11/2000 | Martinez et al. |
| 7,034,127 B2 | 4/2006 | Parent et al. |
| 7,417,021 B2 | 8/2008 | Calias et al. |

FOREIGN PATENT DOCUMENTS

| EP | 0 138 572 A2 | 4/1985 |
| EP | 0216453 A2 | 4/1987 |
| EP | 341745 A1 | 11/1989 |
| EP | 0809996 A2 | 12/1997 |
| EP | 1095064 B1 | 5/2001 |
| EP | 1313772 B1 | 5/2003 |
| EP | 1339753 A2 | 9/2003 |
| EP | 1757314 A1 | 2/2007 |
| WO | WO-98/31345 A1 | 7/1998 |
| WO | WO-02/18448 A2 | 3/2002 |
| WO | WO-2009/001209 A1 | 12/2008 |

OTHER PUBLICATIONS

Pepinsky, R. B. et al., "Improved pharmacokinetic properties of a polyethylene glycol-modified form of interferon-β-1a with preserved in vitro bioactivity," The Journal of Pharmacology and Experimental Therapeutics, 2001, vol. 297, No. 3, pp. 1059-1066.

Motokawa, Keiko et al,, "Selectively crosslinked hyaluronic acid hydrogels for sustained release formulation of erythropoietin," Journal of Biomedical Materials Research Part A, 2006, pp. 459-465.

Bulpitt, P. et al., "New strategy for chemical modification of hyaluronic acid: Preparation of functionalized derivatives and their use in the formation of novel biocompatible hydrogels," Journal of Biomedical Materials Research, Wiley, New York, NY, US, vol. 47, No. 2, Jan. 1, 1999, pp. 152-169.

Bergman, K. et al., "Hyaluronic acid derivatives prepared in aqueous media by triazine-activated amidation," Biomacromolecules Jul. 2007 Amerian Chemical Scoiety US, vol. 8, No. 7, Jul. 2007, pp. 2190-2195.

*Primary Examiner* — Jane Zara
(74) *Attorney, Agent, or Firm* — Birch, Stewart, Kolasch & Birch, LLP

(57) ABSTRACT

The present invention relates to a process for the synthesis of conjugates of glycosaminoglycanes (GAG) with biologically active molecules of varying nature, comprising small molecules and macro-molecules. In particular, the present invention relates to the conjugation of hyaluronic acid (HA) and its derivatives with polypeptides and proteins with a biological action, such as, for example, interferons, erythropoietins, growth factors, insulin, cytokines, antibodies and hormones.

An object of the present invention also relates to isolatable intermediates obtained by the partial or total reaction of GAG with protected amino aldehydes in the conjugation process mentioned above.

28 Claims, 8 Drawing Sheets

Synthesis of aldehydized HA

H-NMR HA aldehydized

PROCESS FOR THE SYNTHESIS OF CONJUGATES OF GLYCOSAMINOGLYCANES (GAG) WITH BIOLOGICALLY ACTIVE MOLECULES, POLYMERIC CONJUGATES AND RELATIVE USES THEREOF

This application is the National Phase Under 35 U.S.C. §371 of PCT International Application No. PCT/EP2010/003634 which has an International filing date of Jun. 4, 2010, which claims priority to Italian Patent Application No. MI2009A 001065 filed on Jun. 16, 2009. The entire contents of all applications listed above are hereby incorporated by reference.

The present invention relates to a process for the synthesis of conjugates of glycosaminoglycanes (GAG) with biologically active molecules of a varying nature, comprising small molecules and macro-molecules. In particular, the present invention relates to the conjugation of hyaluronic acid (HA) and its derivatives with polypeptides and proteins with a biological action, such as interferons, erythropoietins, growth factors, insulin, cytokines, antibodies and hormones.

The use of polymers in the biomedical field is completely general and widespread. Hydrogels with a polymeric base, for example, are commonly used for reducing surgical adherences in abdominal surgery, in reconstruction and cosmetic surgery, in controlled release systems consisting of gelinatous matrixes or as biomaterials.

Another important example is the derivatization of molecules with a pharmacological action with polymeric chains, which improves the solubility and conceals the molecules with respect to degradation processes, prolonging their action.

The most typical example in this context, is polyethylene glycol (PEG) which, although not present in living organisms, is fully biocompatible and not immunogenic. PEG is commonly used for implementing the performances of biological drugs (therapeutic proteins). Pegylated alfa-interferone, or peg-interferon is worth mentioning, for example, which has superseded the simple recombinant version of the protein, becoming the chosen therapy for viral hepatitis as well as a true blockbuster (European patent EP0809996). The limit of the functionalization of proteins with PEG is bound to the attainment of conjugates with irregular functionalization, or, in any case, polydispersed patterns. Furthermore, the various isomers obtained can be characterized by a different biological activity, bio-availability, half-life, immunogenic power.

For this reason, in the nineties', pegylation methods were introduced so as to obtain proteins modified only in specific sites; among these, the N-terminal end is the most accessible as a result of its pKa considerably different with respect to all other amine groups present in the proteins.

In this respect, Pepinsky et al. (Pepinsky R B, Le Page D J, Gill A, et al. *J Pharmac Exp Ther,* 2001 297(3):1059-1066), have specifically studied the introduction of a PEG chain at the N-terminal end of the beta 1 interferon (which is used in the treatment of multiple sclerosis) through reductive alkylation obtained from an aldehyde derivative of PEG. The adduct obtained showed a better efficacy in vivo due the increased half-life.

Another protein which has been modified with PEG thanks to this approach, is G-CSF, a growth factor and activation of neutrophylic granulocytes which Kinstler et al, functionalized at the N-terminal end (U.S. Pat. No. 6,153,655 patent). The corresponding product (Pegfilgrastim) has already been on the market since 2002.

In the group of polymers in the biomedical field, biopolymers are of particular interest. Some of these are naturally present in the human tissues and have properties of biocompatibility and non-immunogenicity, which represent an important added value in this context. Among these biopolymers, glycosaminoglycans (GAG) are of particular interest, i.e. non-branched polysaccharides having a high molecular weight, consisting of disaccharide repetition units. GAGS, for example, have a structural function in the connective tissue, tendons and cartilage or they can act as anticoagulants.

Hyaluronic acid (HA) is a GAG which can be found in the extra-cellular matrix with a structural role involved in the cell motility process but also has visco-elastic function in addition to being a hydrating and proliferation agent, Thanks to these particular characteristics, HA and its derivatives are used as matrix for bio-materials (EP 216453) and controlled release systems (U.S. Pat. No. 4,582,865 & U.S. Pat. No. 4,636,524; K. Motokawa et. al., *Journal of Biomedical Materials Research Part A*, (2006), pag. 459).

HA is also involved in molecular recognition and regulation mechanisms, as it is recognized by cell receptors such as RHAMM (CD168), CD44, LYVE1, Layilin. The interaction specificity of HA with CD44 is of particular importance. This receptor, in fact, is overexpressed in the majority of solid cancers of an epithelial origin; by binding drugs having an anti-cancer activity to HA, the active targeting of the biopolymer can be exploited, which allows the endocytosis and release of the anti-cancer agent inside the neoplastic cell (international patent application WO2009001209).

The derivatization of therapeutic agents with hydrosoluble polymers (as, for example, GAG) is particularly useful in the case of polypeptides, polypeptide hormones and proteins. This class of molecules, in fact, has a structure which is extremely susceptible to even small modifications, caused by the environment in which they are present. Furthermore, polypeptides and proteins normally have an efficacy time span very limited by their short half-life. This is why their functionalization with hydrosoluble polymers is extremely important, also improving the solubility, bio-availability and reducing the immunogenicity.

Conjugation methods of GAG with proteins through divinyl sulfone (U.S. Pat. No. 7,034,127 which particularly refers to IFN), disulphide bridges (U.S. Pat. No. 7,417,021), are known in the art. The only method which allows the control of the derivatization site is the reaction through the formation of disulphide bridges; in this case the polymer can only bind itself in correspondence with residues of cysteine in a reduced form.

If the polypeptide chain only has one single cysteine residue available, and in reduced form, the derivatization method is in fact specific, but this is quite a rare case. Proteins, in fact, often have numerous cysteine residues, but, above all, it often happens that these residues are already engaged in disulfide bridges whose reduction involves significant rearrangements which can lead to the loss of the functionality of the protein.

None of the methods of the known art allows a univocal functionalization pattern to be obtained, even maintaining the biological activity of the protein, therefore an effectively mono-dispersed and efficient product.

On the basis of the above, the necessity of availing of a conjugation process of bioactive molecules, such as proteins and polypeptides, to GAG (i.e. HA) without compromising the protein functionality, is evident.

The authors of the present invention have now set up a conjugation process of glycosaminoglycanes having biologically active molecules (i.e. proteins and polypeptides)

capable of overcoming the limits of the prior art, as it allows GAGs (such as HA) to be bound with no modification of the basic structure of the protein and jeopardizing its functionality. A further characteristic which distinguishes the conjugates between GAG and a therapeutic agent (TA) of the present invention with respect to the conjugates known in the state of the art, consists in the fact that the present conjugation method leads to the formation of an almost mono-dispersed adduct and not to an isomeric mixture of products with different chemical, physical, biological characteristics, whose behaviour, therapeutic efficacy and toxicological profile are variable.

Furthermore, by suitably varying some of the process parameters (i.e. pH), it is also possible to select the amine groups of the biologically active molecule to which the glycosaminoglycane is bound; it is possible, for example, to specifically bind the hydrosoluble polymer HA to the N-terminal end.

In the case of drugs such as proteins and polypeptides, the coupling to the amine group often takes place through acylation, which leads to the formation of amides, whose nitrogen is no longer capable of participating in acid-base equilibria.

The conjugation method of the present invention is characterized in that it does not imply any alteration of the net charge present in the active species, which leads to the transformation of a primary amine to a secondary amine that maintains the capacity of exchanging protons. This is a clear advantage in terms of maintenance of the biological activity of TA.

Even more surprisingly, the authors of the invention have discovered that the bio conjugates of the present invention are capable of increasing the efficacy of the conjugated drug and to maintaining it with time (see Example 10 HA conjugate-insulin).

The conjugation of the therapeutic agent with the hydrosoluble polymer, improves it characteristics, making it more soluble, bio-available and more active, Unlike the hydrosoluble polymers described in the state of the art (such as, for example, polyethylene glycol, PEG), the use of glycosaminoglycanes allows excellent drug delivery systems to be obtained, which are capable of directing the therapeutic agent with a specificity inaccessible with other types of polymers. This specificity is determined by the complex system of receptor interactions which involve GAGs. Furthermore, the use of biopolymers which, although interacting with the cell receptors, do not promote an immunological response, results in a synergetic action with a higher efficacy.

The present invention describes a process for the synthesis of conjugates of glycosaminoglycanes (GAG) with biologically active molecules, comprising the following phases:
a) derivatization of the GAG with at least one aldehyde group (CHO), by reaction of the GAG with a spacer molecule (SP), wherein said spacer molecule comprises, as first functional group, one or more aldehyde groups (SP-CHO), said aldehyde groups (SP-(CHO)) being optionally protected and, as second functional group, a nucleophilic group suitable for conjugation with the GAG;
a1) hydrolysis of the activated intermediate with aqueous acids when said one or more aldehyde group(s) is protected;
b) reaction of the adduct obtained in phase a) or a1) with at least one biologically active molecule (TA) characterized in that it comprises a functional group capable of reacting with the aldehyde group.

Hydrogels consisting of hyaluronic acid functionalized with amine or aldehyde groups (protected or non-protected) are known in the state of the art, these derivatives, however, are subsequently cross-linked with other molecules of the same polysaccharide possibly derivatized with different functional groups which are such as to react with the amine or aldehyde group of the starting functionalized hyaluronic acid (EP1757314; Bulpitt P, et al. *J of Biomedical Materials Research*, 1999 47(2):152-169).

As already mentioned, glycosaminoglycanes (GAGs), are non-branched polysaccharides having a high molecular weight, consisting of disaccharide repetition units. A common characteristic of GAGs is the presence of a carboxylic functional group per disaccharide unit, which can appear in nature in acid or salified form, thus generating polyanions. In the present invention, the acronym GAG indifferently indicates the acid form or the salified form of polysaccharides, and in this case the most typical counter-ions are alkaline and alkaline-earth metals, such as sodium, potassium, magnesium, calcium. Polymers classified as GAG, comprise: hyaluronic acid, condroitin sulphate, dermatan sulphate, keratan sulphate, heparin, heparan sulphate. The GAGs to be used within the present invention can be in native form or in the form of semi synthetic derivatives including quaternary ammonium salts, carboxylic esters, O-esters, amides, percarboxylated derivatives, O-sulfated derivatives, N-deacetylated derivatives, N-sulfated derivatives, or mixed derivatives characterized by the simultaneous presence of these modifications. The acronym GAG is used hereinafter to indicate both the mentioned polymers in native form or the corresponding semisynthetic derivatives.

Even if GAGs, in normal representations as structure formulae, do not carry any aldehyde group, it is worth remembering that the natural equilibrium which is established in the solution between the open form and the closed form of the reducing end, passes through the formation of a functional aldehyde group. This presence is quantitatively extremely limited, however, as the length of the polymeric chains creates a low quantity of reducing ends. When the molecular weight of the GAG diminishes, on the other hand, the relevant quantity of reducing ends available in aldehyde form progressively increases, until it becomes quantitatively useful for the oligomers of GAGs; this is the only case in which the reducing ends can be efficaciously used for effecting the conjugation process described in this document.

In all other cases, considering that the aldehyde group is rather unstable even under mild conditions, it is convenient to introduce it synthetically into the hydrosoluble polymer in the form of protected aldehyde. In this way, it is possible to isolate an activated intermediate which is subsequently reacted with the TA, without having to put all the components in contact in a single reaction mixture.

The conjugates according to the present invention are linked in that the therapeutic agent TA is bound to the hydrosoluble polymer as secondary or tertiary amine. The presence of the aldehyde group (possibly protected as described in phase a)), as a means for enabling the bond between the therapeutic agent and GAG, and the synthesis method prepared by the Applicant and illustrated in the present document should be considered as being the characteristic feature of the present invention.

The adduct thus obtained in phase a) is stable enough to allow it to be isolated, but once the aldehyde groups have been released, it is available with respect to the derivatization reaction with the therapeutic agent of interest.

The conjugate obtained can be described by the following general formula:

wherein GAG indicates the Glycosaminoglycane, SP a spacer arm and TA the therapeutic agent.

Translating the symbology of this derivatization method, the following is obtained:

GAG+SP-(CHO)→GAG-SP-(CHO)   Phase a.

GAG-SP-(CHO)→GAG-SP-CHO   Phase a1.

GAG-SP-CHO+TA→GAG-SP-TA   Phase b.

wherein CHO indicates the functional aldehyde group, protected if between brackets.

This protection can be easily obtained with the organic synthesis techniques known to experts in the field. A convenient form of protection, for example, consists in the use of hemiacetals or acetals, obtained through the reaction of aldehydes with aliphatic or aryl aliphatic alcohols or diols, comprising for example, methanol, ethanol, n-propanol, isopropanol, n-butanol, sec-butanol, tert-butanol, iso-butanol, ethylene glycol, propylene glycol, 1,3-propandiol, 1,4-butandiol and structurally similar molecules, and capable of reacting with the aldehydes to form isolatable acetals. The product of phase (a) represents what is defined as "activated intermediate" or "activated but isolatable semisynthetic intermediate".

The chemistry used for the functionalization of GAG with the spacer arm to obtain the activated intermediate can be selected each time using the functional groups present in the polymer or in the corresponding semisynthetic derivative, i.e. the carboxylic group, hydroxyl groups (4 for each repetitive unit), sometimes present in the form of alkyl or O-sulfated esters, the N-acetyl group, the N-sulfated group. Furthermore, the coupling conditions between the GAG and spacer arm must be such as to not alter the aldehyde group, or remove its protection when present.

The spacer arm must contain a functional group suitable for the covalent union with the GAG, preferably a nucleophilic such as, for example, an amine or alcohol group. The amine group, in free form or salified with suitable salts is preferred for its greater nucleophilicity. The spacer molecule SP-(CHO) is preferably an amino-aldehyde, even more preferably protected as acetal.

Examples of molecules which can be used as spacer arm of the GAG-SP-(CHO) type comprise amino-aldehyde acetals thus composed:

Amine group, free or in the form of a salt

A hydrocarbon chain, preferably aliphatic with a number of carbon atoms ranging from 1 to 20

An aldehyde group, preferably in the form of an acetal according to the following scheme, in which n ranges from 1 to 20 whereas R and R' can be aliphatic or aryl-aliphatic residues, the same or different, or the same chain which carries various hydroxyl groups

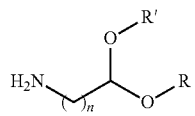

The aliphatic chain, in addition to being linear as schematized, can be branched, or contain aryl groups.

The Applicant has verified that a convenient coupling method consists in the formation of amides, in which the GAG participates as carboxylic acid, and the spacer arm as amine. This type of reaction is effected according to organic synthesis techniques known to experts in the field, and can be carried out for example with the help of condensing agents which promote the nucleophilic attack towards the carboxylic acids. These reagents include those which can be used in the peptide synthesis in homogeneous or heterogeneous phase. Examples of these agents are carbonyl diimidazole, di-succinimidyl carbonate, carbodiimmides such as, for example, 1-ethyl-3-(3-dimethylaminopropyl) carbodiimide (EDC); N,N'-dicyclohexylcarbodiimide; N-allyl-N'-(β-hydroxyethyl) carbodiimide; N-(α-dimethylaminopropyl-N'-tert-butylcarbodiimide; N-(α-dimethylaminopropyl)-N'-(β-bromoallyl) carbodiimide; 1-(3-dimethylaminopropyl)-3-(6-benzoylaminohexyl) carbodiimide; Cyclohexyl methylmorpholine) ethyl carbodiimide p-toluenesulfonate (CMC) and similar products.

The reaction can be carried out in an aqueous medium or in an organic solvent at a temperature ranging from −10 to 70° C. depending on the type of activation used. When the preparation is carried out in a non-aqueous medium, it is convenient to use GAG salts which are more soluble under these conditions, for example tetra-alkylammonium salts. These counterions must in any case be eliminated by means of the ion exchange process, to be effected on the derivatized polymer before its isolation.

The tetra-alkylammonium salts of GAG (in particular of HA) are normally soluble in aprotic polar solvents, such as N-methyl-pyrrolidone (NMP), dimethylsulfoxide (DMSO), dimethylformamide (DMF), which are suitable as reaction medium. The use of these solvents is conveniently coupled with the use of carbonyl diimidazole as condensing agent, whose action is favoured by a slightly acid environment for small quantities of strong acids, for example gaseous hydrochloric acid bubbled in solution or methane-sulfonic acid. Other organic solvents suitable for effecting this type of synthesis of the activated intermediate are organic carbonates, comprising propylene carbonate, diethyl carbonate, and in general organic carbonates substituted by aliphatic, aromatic or aryl-aliphatic chains.

The reaction is interrupted by the addition of a saturated solution of an alkaline halide, for example NaCl, NaBr, KCl, KBr. The hydration of the reaction mixture deactivates the promoters of the formation of amide bonds, whereas the salt, added in such a quantity as to be in strong excess with respect to the moles of repetitive unit of GAG, causes an effective ion exchange. The stoichiometric requirement of the strong excess is obtained by adding a quantity of saturated solution of alkaline halide ranging from 0.5% to 30% by volume, and preferably from 5 to 15% by volume.

The corresponding alkaline salt of the activated intermediate is subsequently purified by dialysis, then freeze-dried. Although this product is isolatable and stable, it is active with respect to the subsequent functionalization reaction with therapeutic agents containing functional groups susceptible to reaction towards the aldehydes.

An alternative purification/isolation method of the activated intermediate consists in applying precipitation-washing cycles with mixtures of solvents having an adequate polarity. The precipitation-washing can be effected, for example, with alcohols such as methanol, ethanol, n-propanol, isopropanol and higher homologues, possibly mixed with water; other suitable solvents are acetone, ethyl acetate, tetrahydrofuran, dioxane, acetonitrile, aprotic polar solvents (for example dimethylformamide, dimethylsulfoxide, n-methyl pyrrolidone, n-methylacetamide), organic carbonates. Each of the mentioned solvents can be used alone or in a mixture with any other solvent or with water in order to obtain the polarity and other physico-chemical characteristics with greater accuracy. Mixtures comprising the above alcohols, acetone and water are preferred.

Phase (b) which describes the coupling between the GAG-SP-(CHO) and TA takes place through a first phase a1) for releasing the aldehyde group (when protected), which consists in hydrolysis of the acetal which is effected by treatment with aqueous acids according to the standard techniques known to experts in the field.

Said hydrolysis phase a1) with aqueous acids of the activated intermediates to release the aldehyde group preferably takes place at a pH ranging from 1.5 to 3.0, preferably with a pH ranging from 2.0 to 2.5, at a temperature ranging from 25 to 65° C., preferably from 40 to 60° C., for at least 30 minutes.

The free aldehyde is now susceptible to nucleophilic attack on the part of the therapeutic agent, activated through the amine group present in the TA molecule, which leads to the formation of an imine, reduced to amine through the inorganic hydrides typically used in reductive amination reactions, for example cyanoboron hydride, lithium aluminum hydride, sodium boron hydride and the like.

The active principles with a pharmaceutical action of interest within the scope of the present invention comprise, for example, "small molecules" with a pharmacological action, and/or polypeptides, hormones, proteins, glycoproteins, enzymes, cytokines, growth factors or cell differentiation factors, antibodies, therapeutic polymers, nucleic acids, or a combination thereof. According to preferred embodiments of the present invention, the "active species" which can be conjugated to HA with the technique described in the present invention comprise:

Polypeptides and/or Proteins, in particular:

Immunomodulators, in particular proteins belonging to the family of interferons, such as, for example, interferons of type I i.e. those which bind themselves to the same receptor of IFNα, which in addition to IFNα comprise IFNβ and IFNω; interferons of type II and type III, i.e. interferons which bind themselves to the receptor of IFNγ and IFNλ, respectively.

Growth factors, in particular;
1. Erythropoetins and in general molecules identified as ESA (Erythropoiesis-Stimulating Agent), comprising epoetin α and epoetin β, epoetin ω epoetin δ, darbepoetin, CERA, and substances generated or deriving therefrom, such as fusion proteins by the stimulation of erythropoiesis;
2. Factors which stimulate haematopoiesis, such as GM-CSF G-CSF factors, which can also be used in the oncological field;
3. Growth factors for bones and cartilages comprising proteins belonging to the Bone Morphogenetic Protein (BMP) family such as, for example, BMP1, BMP2, BMP3, BMP4, BMP5, BMP6, BMP7 (also indicated in literature as OP1), BMP8a, BMP8b, BMP10, BMP15, BMP9 also known as GDF2 (Growth Differentiation Factor 2), proteins belonging to the super-family of TGF-beta, VEGF, PDGF, proteins belonging to the FGF family;

Cytokines and their receptor antagonists, such as, for example, IL2, TNF with their soluble receptors or correlated monoclonal antibodies; IL1-ra (IL1-receptor antagonist, for the treatment of arthritis and rheumatoid arthritis) and, in general, soluble receptors of pro-inflammatory cytokines;

Glycoproteins, in particular Lubricin;

Enzymes: in particular Dismutase superoxide (SOD); Ribonuclease and Glucocerebrosidase;

Antibodies: in particular monoclonal antibodies or their conjugates or fusion proteins; Monoclonal antibodies which exert an anti-tumoral action; Monoclonal antibodies which exert an anti-inflammatory action;

Hormones: protein hormones or at least partially containing a polypeptide chain, in particular Calcitonin, Insulin and its analogues, and the growth hormone (GH or hGH), Therapeutic agents containing amine groups not fundamental for biological functioning:

Anti-tumoral drugs, in particular:
1. Taxans, Vinca alkaloids; Camptothecins;
2. Substituted Ureas;
3. Complexes of platinum, gold, silver and other metals used for example in therapy of tumors or osteoarthritis and/or rheumatoid arthritis, or bacteriostatic/antibacterial agents;
4. Methotrexate, trimetrexate, pemetrexed, tetrahydro-folate;
5. Analogues of pyrimidine; cytidine, purine;
6. Oncological antibiotics and analogues; Anthracene-diones;

Antiviral agents and antibiotics;
Protease and polymerase inhibitors;
Anti-inflammatory, analgesic, anaesthetic, anti-pain drugs with a central or peripheral action;
Narcotics opiate or non-opiate;
Steroids;
Minoxidyl (normally used in dermatology).

Nucleic acids, in particular
1. small interfering RNA (or short interfering RNA, commonly known as siRNA, this is an RNA molecule between 20 and 25 nucleotides long. More specifically, siRNAs are involved in the inhibition of the expression of single genes, their use for the treatment of macular degeneration is currently in experimental phase).
2. MicroRNAs (microRNAs, miRNAs, are small non-encoding RNA molecules which modulate the expression of specific target genes. They can therefore function as tumor suppressors on specific malign hemopoietic forms).
3. antisense RNA The substances listed above are indicated hereafter as "therapeutic agents" (abbreviated TA) or "active species".

The molecular structure of the TA must carry a functional group capable of reacting with aldehydes, for example an amine group. If this group is not present in the TA, it can be introduced by means of synthetic organic chemistry techniques known to experts in the field. In this way, it is possible to virtually bind any molecule to GAG.

Within the scope of the present invention, the use of hyaluronic acid (HA) and its salts indicated above, is of particular interest. The HA used in the present invention can derive from any source; it can be produced, for example, by extraction of cockscombs, fermentatively, or biotechnologically, and have a molecular weight ranging from 400 to $3 \times 10^6$ Da, preferably from $1 \times 10^3$ Da to $1 \times 10^6$ Da, even more preferably from 10,000 to 750,000 Da.

The derivatization reaction of the invention can be applied to both the polysaccharide as such and to the same previously modified. Molecular networks are thus obtained starting from hyaluronic acid variably modified according to known methods and in particular:

HA salified with organic and/or inorganic bases (EP 138572 B1);

HYAFF®: esters of HA with alcohols of the aliphatic, aryl-aliphatic, cycloaliphatic, aromatic, cyclic and heterocyclic series, with an esterification percentage which can vary according to the type and length of the alcohol used, preferably from 20 to 80%, whereas the remaining percentage of non-esterified HA can be salified with organic and/or inorganic bases (EP 216453);

HYADD®: amides of HA with amines of the aliphatic, ar-aliphatic, cycloaliphatic, aromatic, cyclic and heterocyclic series, with an amidation percentage of 0.1 to 50%, whereas the remaining percentage of HA not subjected to amidation can be salified with organic and/or inorganic bases (EP 1095064);

O-sulfated derivatives of HA up to the 4$^{th}$ degree of sulfation (EP 702699);

ACP®: internal esters of HA with an esterification percentage not higher than 20%, preferably from 0.05 to 10% of esterification, whereas the remaining percentage of non-esterified HA can be salified with organic and/or inorganic bases (EP 341745);

deacetylates of HA: these derive from the deacetylation of the N-acetyl-glucosamine residues present in HA, with a deacetylation percentage preferably ranging from 0.1 to 30%, whereas all the carboxylic groups of HA can be salified with organic and/or inorganic bases (EP 1313772);

HYOXX™: percarboxylate derivatives of HA obtained from the oxidation of the primary hydroxyl of the N-acetyl-glucosamine fraction with a percarboxylation degree of 0.1 to 100% and preferably from 25 to 75%. All the carboxylic groups of HA can be salified with organic and/or inorganic bases (EP 1339753).

According to a preferred embodiment of the invention, the conjugation process between HA and therapeutic agents comprises the following phases:

a) derivatization reaction of HA with protected amino-aldehydes SP-(CHO) in which HA participates in the reaction with the carboxylic group which forms an amide with the amine of the amino-aldehyde. This passage is preferably carried outfrom starting HATBA (tetrabutylamonium salt of HA) or another salt soluble in an organic aprotic polar solvent (DMSO, NMP, DMF, organic carbonates). The activated but isolatable intermediate (which is a further object of the invention, QUESTA ERASE é DA TOGLIERE) is obtained from this passage.

a1) hydrolysis of the activated intermediate i.e. HA-SP-(CHO)→HA-SP-CHO to release the aldehyde group: reaction with phosphoric acid within a pH range of 1.5-3, preferably with a pH ranging from 2.0 to 2.5, at a temperature ranging from 25 to 65° C., preferably from 40° C. to 60° C., for at least 30 minutes;

b) conjugation reaction of the activated intermediate with the TA molecule, preferably a protein. By adding the protein under reducing conditions with sodium cyanoborohydride, there is the formation of imine and therefore an amine. If the therapeutic agent selected is a polyfunctional compound, there is the possibility of creating different positional isomers with different chemical, physical and biological characteristics. This condition is typically verified in the case of proteins, of which interferon, which has 12 potential binding sites, represents an example. By changing the pH at which this reaction is effected, a specific functionalization is preferably generated at the N-terminal (pH=6.0) with all the advantages that this implies or a functionalization with HA bound to the protein in various points, with a non-reproducible scheme (pH≥7.5).

The chemistry used for preparing the conjugates according to the present invention allows the functionalization pattern to be effectively selected.

This important result is reached thanks to the use of the aldehyde group, whose particular reactivity with respect to nucleophilic attacks enables a sufficient selectivity with respect to the nucleophilic power of the ingoing group. The specific conditions for conveniently exerting this selectivity are determined from case to case through progressive optimizations. Returning to the example of the most important polyfunctional active species, i.e. the proteins, the nucleophilic amine groups can be found in positions having different accessibilities, but above all can be distinguished with respect to their strength as bases, expressed as pKa. The amine groups in a position present in the lysine residues typically show a pKa ranging from 9.3 to 9.5, whereas the amine groups in α at the carboxyl have a pKa typically ranging from 7.6 to 8. In order to favour the reaction of the amines in ε the coupling process must be carried out at a pH higher than 8.0, preferably ranging from 8.5 to 9.0; in order to favour the reactivity of the amines at the N-terminal, on the other hand, the pH must be within the range of 5.0 and 6.5, and preferably between 5.5 and 6.2. This second case is the most important as the proteins typically have only one free α-amine group, situated at the N-terminal end. Establishing the reaction conditions so as to prevalently react this amine group leads to the formation of an almost monodispersed conjugate between GAG and proteins.

Although the pH values indicated mostly represent the proteins of interest for the present invention, they are indicative as they may shift slightly for different molecules.

This synthesis procedure allows bioactive conjugates to be obtained, having substantially higher performances with respect to the conjugates known in the state of the art. By studying the biological properties of these new conjugates, the Applicant has in fact found substantially higher characteristics with respect to the polymeric conjugates known in the state of the art.

In particular, the conjugates of the invention obtained after derivatization with hyaluronic acid maintain the biological properties of both the active principle and starting polysaccharide, but they are characterized by different mechanical and rheological properties. The conditions under which the coupling process is effected are such as to not modify the biological functionality of the TA.

The applicant has in fact applied the synthesis process according to the present invention for synthesizing new bioconjugates:

between hyaluronic acid (HA) and interferon (IFNα)
between hyaluronic acid and the growth hormone (hCH)
between hyaluronic acid (HA) and RNAse A
between hyaluronic acid and insulin,
between hyaluronic acid and salmon calcitonin (HA-sCT)
between hyaluronic acid and IL1-ra
between hyaluronic acid and Lubricin, which are therefore an object of the present invention.

The preparation of the HA-IFNα conjugate is described in Example 3. Recombinant human IFN alpha 2a is a protein having a molecular weight of about 20 kDa whose structure is characterized by 4 cysteines which form 2 disulfide bridges and 12 amine groups, of which 11 in the side chain of lysine residues, plus the N-terminal end. It should be noted that of the two disulfide bridges present in the native protein, that included between the residues 29 and 138 is fundamental for the biological activity, consequently the reducing conditions necessary for applying the method according to U.S. Pat. No. 7,417,021 would be destructive.

The synthesis conditions used are such as to obtain an almost monodispersed conjugate, with the HA prevalently bound to the N-terminal end of the cytokine. This specificity is reflected on a maintenance and/or increase of the biological activity of the IFN and/or other bioconjugates, for whose measurement the method according to Example 4 has been developed.

Fluorescence tomography experiments were effected on the same HA-IFN conjugate, to observe the biodistribution in vivo following endovenous administration. In order to allow it to be revealed with this technique, the bioconjugate was prepared according to Example 6, so as to include a covalently bound fluorescent probe. The biodistribution profile found (Example 7) shows that in a rather rapid time scale, the fluorescence prevalently accumulates at a hepatic level, and to a lesser extent in the chest area, due to non-specific entrapment in the pulmonary microcirculation. In more lengthy times, an accumulation in the pelvic, in particular vesical region is also observed, justified not so much by the normal absorption-excretion mechanism of the bioconjugate, but by the slow hydrolysis and release of the fluorescent probe. The evidence of this substantial hepatic and pulmonary accumulation reveals a further interesting property, which is not presented by the conjugates known in the state of the art, i.e. the possibility of directing the therapeutic species specifically to certain types of tissue.

A further object of the invention therefore relates to the use in the medical field of the conjugates according to the invention, in particular in antiviral and antitumoral therapy. According to a preferred embodiment, an object of the invention relates to the use of the HA-IFN conjugate as a system for stimulating the immune system with respect to viral-type infections, such as hepatitis (preferably by endovenous administration) or pathologies caused by viral agents, such as, for example, herpes labialis, genitalis, and in infections caused by HPV (Human Papilloma virus) capable of causing verrucas (preferably by topic application) or cervix cancer. The HA-IFN conjugate can therefore also be advantageously used as antitumoral agent.

As shown in Example 10, the HA-insulin conjugate not only doubly increases the pharmacological efficacy of the therapeutic agent, but it also maintains the capacity of the insulin of controlling the basal glucose level with time. In this case, a further property of the bioconjugate is revealed, which consists in creating controlled release systems of therapeutic agents.

In Example 9 which illustrates the preparation of the bioconjugate HA-RNAse A, the maintenance of the biological activity of the bound enzyme is even more evident, as the measurement of the enzymatic activity is effected, directly following the concentration of the substrate with spectroscopic techniques.

The applicant also verified that, once conjugated to HA and administered endovenously, the therapeutic agent shows a rapid and quantitative hepatic and pulmonary accumulation. This aspect of the invention makes its use particularly advantageous in therapies relating to pathologies which interest the liver, such as for example, virus-correlated hepatopathies, hepatic fibrosis, cirrhosis of the liver, Gaucher's disease, liver and lung tumors. The kinetics and effectiveness of the hepatic and pulmonary entrapment of the conjugate depend on the HA, by modifying its molecular weight, the accumulation profile can be modified until it becomes negligible.

Endovenous administration, on the other hand, is not the only possible way. The Applicant has in fact verified that subcutaneous administration of the conjugate is effective in slowly releasing the TA (Example 10).

Example 11 illustrates the preparation process of the bioconjugate HA-calcitonin: calcitonin is a 32-amino acid linear polypeptide hormone that is produced in humans primarily by the parafollicular cells of the thyroid, this hormone participates in calcium ($Ca^{2+}$) and phosphorus metabolism. To be specific, calcitonin affects blood $Ca^{2+}$ levels in four ways:

Inhibits $Ca^{2+}$ absorption by the intestines
Inhibits osteoclast activity in bones
Inhibits phosphate reabsorption by the kidney tubules
Increases absolute $Ca^{2+}$ and $Mg^{2+}$ reabsorption by the kidney tubules, calcitonin is a renal Ca-conserving hormone.

Therefore, calcitonin is used for the treatment of:
Postmenopausal osteoporosis
Hypocalcaemia
Paget's disease
Bone metastases Calcitonin has short absorption and elimination half-lives of 10-15 minutes and 50-80 minutes, respectively. Salmon calcitonin is primarily and almost exclusively degraded in the kidneys, forming pharmacologically-inactive fragments of the molecule.

The new bioconjugate HA-calcitonin is therefore extremely important, due to the fact that, as described in Example 11, it reveals a more prolonged hypocalcemizing action with respect to the free hormone, allowing a more marked effect which enables us to study new clinical uses such as intra-articular administration for the protection of the cartilages and bones in degenerative pathologies such as Rheumatoid Arthritis and arthrosis.

Example 13 illustrates the synthesis process of the bioconjugate HA-Lubricin: lubricin is present in synovial fluid and on the surface of articular cartilage and therefore plays an important role in joint lubrication and synovial homeostasis. Human synovial fibroblasts have been shown to produce lubricin.

Optimal functionality of synovial joints is dependent upon extremely low coefficients of friction between articulating tissues. Normally, a contiguous, well-lubricated surface is maintained on articular cartilage. During osteoarthritis (OA), however, reduced lubrication contributes to cartilage matrix degradation and fibrillation; these in turn contribute to joint dysfunction and pain. Reduced lubrication also leads to joint dysfunction and pain in other forms of arthritis, including rheumatoid arthritis (RA). The expression of lubricin has also been detected and the protein localised in tendon, meniscus, lung, liver, heart, bone, ligament, muscle and skin.

For these tissues a lubricated surface also contributes to optimal functionality. In addition to requiring a lubricated surface, normal tendon function requires the prevention of cellular adhesion to tendon surfaces.

Therefore, the Applicant is describing the new use for the new bioconjugate HA-lubricin, as lubricants, anti-adhesive agents and/or intra-articular supplements for, e.g., synovial joints, meniscus, tendon, peritoneum, pericardium and pleura, allowing a residence time in situ and a higher effectiveness than that described for non-conjugated TAs.

In this context, the conjugates according to the present invention can be advantageously used as systems for the controlled release of TAs. These systems are extremely useful for TAs which have a therapeutic effectiveness window limited by a restricted lifetime. Typical examples of TAs having these characteristics are therapeutic proteins, comprising cytokines, growth factors, enzymes, hormones, such as for example GH, Glucocerebrosidase, SOD, IL1-ra, insulin and analogues, GM-CSF, GCSF, FPO and in general the ESAs described above, interferons of type I, II, III, monoclonal antibodies, fusion proteins and others. Insulin, for example was the first biotechnological drug and continues to have primary importance as it is fundamental for the growing number of people suffering from diabetes. Retard forms of insulin are currently available, but drug-delivery systems are not present on the market (conjugation to polymers, micro-nanoparticles).

As shown in Example 10, the conjugation method according to the present invention is suitable for creating controlled release systems which are effective in slowly releasing the TA in active form, and prolonging the action, doubling its therapeutic effectiveness. Also to be taken into account is the further aspect relating to the compliance of the patients who in the present therapeutic regime must undergo various daily subcutaneous administrations with evident inconveniences in their social life and in the progressive exhaustion of sites suitable for the injection. Analogous considerations are also valid for the other therapeutic substances listed in the present document.

The conjugates between hyaluronic acid (preferably its derivatives) and therapeutic agents according to the present invention can therefore be advantageously used for the preparation of biomaterials with higher characteristics of effectiveness, biocompatibility, bioavailability, the possibility of directing the TA to specific types of cell or organ tissues, and the possibility of improving the pharmacokinetic profile by the controlled release and increased lifetime of the TA.

The conjugates between hyaluronic acid and therapeutic agents according to the present invention can be advantageously used for the preparation of pharmaceutical compositions suitable for parenteral or non-parenteral administration, comprising formulations for oral use, injectable solutions by intradermal, endovenous, intramuscular, subcutaneous, (intradermal da toglire, scritto 2 volte!), intra-arterial, intrathecal, intracardiac, intrasynovial, intraperitoneal, intravesical injection, or gels, creams, ointments, foams, dry powder, sprays, cutaneous or transdermal plasters for topic use, but also pharmaceutical preparations for rectal, intravaginal, sublingual, intraocular use.

According to a preferred embodiment of the present invention, the pharmaceutical compositions are suitable for endovenous administration for a hepatic and/or pulmonary localization. According to a further preferred embodiment, the pharmaceutical compositions are suitable for subcutaneous administration by means of controlled release systems.

The conjugates according to the invention maintain the biological function of the active principles contained therein, but with respect to the isolated form of these, they can be used as systems for their vehiculation and controlled release. The vehiculation towards specific tissues or types of cells is obtained by suitably selecting the type of GAG or semisynthetic derivative, whereas the release kinetics is modulated through the nature of the bond between the GAG or semisynthetic derivative and active species.

Finally, the invention relates to a biomaterial characterized by a matrix comprising the conjugates as defined above.

The present invention is now described for illustrative but non-limiting purposes, according to its preferred embodiments with particular reference to the figures of the enclosed drawings, in which:

FIG. 1 shows the synthesis scheme of the aldehydized GAG, represented for illustrative purposes by hyaluronic acid (HA), whereas the spacer arm prototype which carries the protected aldehyde group represented is 4-amino-butyraldeide-diacetal.

FIG. 2 shows the H-NMR spectrum of aldehydized hyaluronic acid. This is a proton NMR spectrum registered in deuterated water. The signal of the methyl proton of the acetyl group present in HA (1.88 ppm) is flanked by a further signal to be attributed to the methyl proton of the acetal (1.05 ppm).

Figure 11:
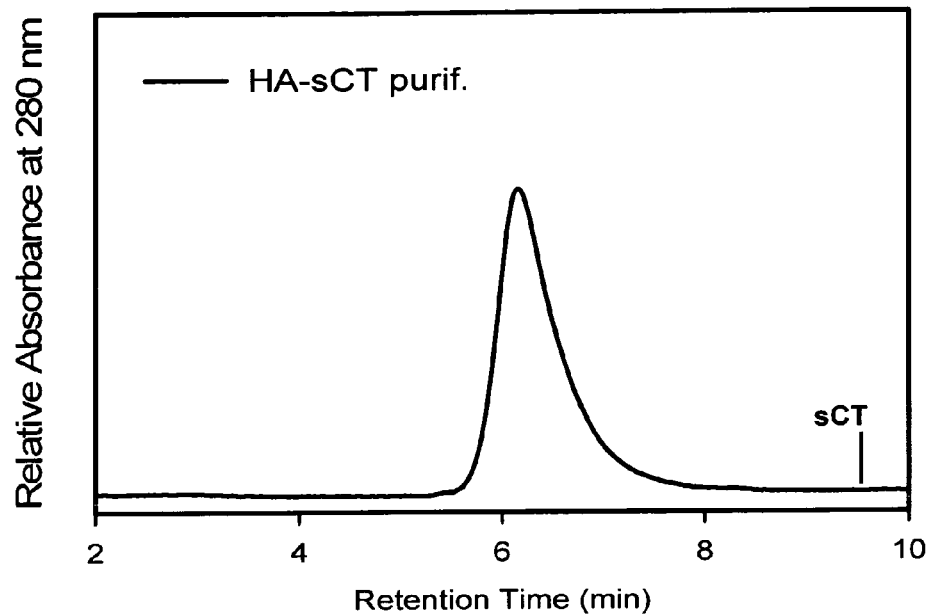

FIG. 11 shows the dimensional exclusion analysis of HA-sCT using a GF-250 column (Agilent, 4.6×25 cm) at a flow of 0.3 mL/min. Eluent: buffer $Na_2HPO_4$ 0.1M, NaCl 0.2M, pH 7.2 containing 20% of acetonitrile. The effluent from the column was monitored by measuring the absorbance at 280 nm. The calcitonin which elutes at 9.2 min was completely removed. The run buffer was injected to demonstrate that the peak at 11 min corresponds to the end of the separation volume of the column used.

Figure 12:
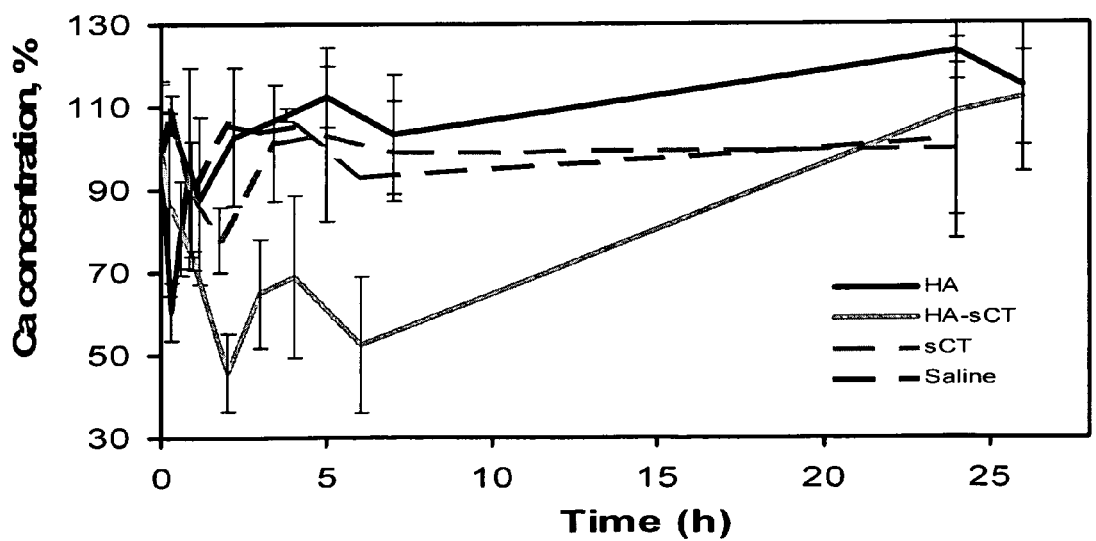

FIG. 12 represents the profile of the calcium level in the blood after e.v. administration of sCT, HA-sCT, HA and saline solution. The data represent the average of three rats and are represented with the relative averages of the standard deviations.

Figure 13:
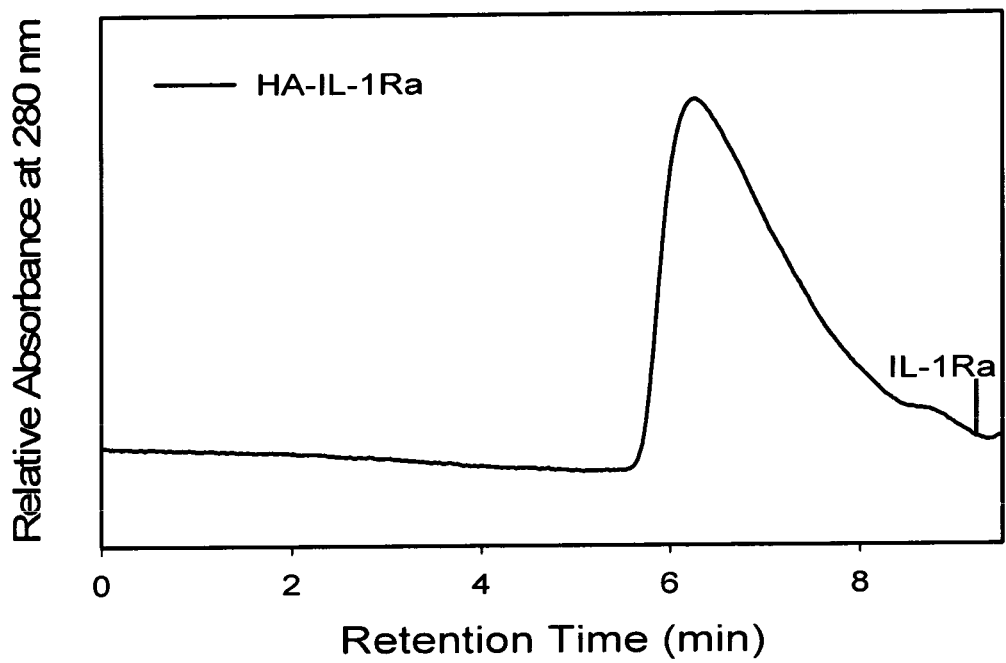

FIG. 13 shows the dimensional exclusion analysis of HA-IL1-ra using a GF-250 column (Agilent, 4.6×25 cm) at a flow of 0.3 mL/min. Eluent: buffer $Na_2HPO_4$ 0.1M, NaCl 0.2M, pH 7.2 containing 20% of acetonitrile. The effluent from the column was monitored by measuring the absorbance at 280 nm. The IL-1-ra which elutes at 9.75 min was completely removed.

The invention is now described in greater detail in the following examples, for the purpose, without limiting its possible applications, of providing a better understanding and illustrating possible embodiments thereof, which can in any case be varied by experts in the field without jeopardizing its basic spirit.

EXAMPLES

Figure 1:
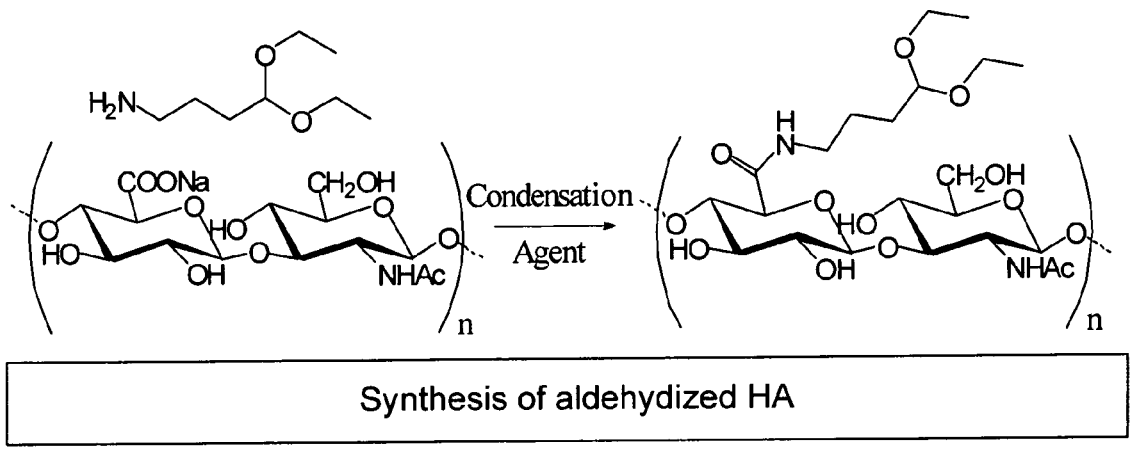

The scheme in FIG. 1 illustrates the succession of reactions of the synthesis process of GAG-TA conjugates described above, describing the molecular structure of the species involved. Hyaluronic acid (HA) is represented for illustrative purposes as GAG, whereas the spacer arm prototype which carries the protected aldehyde group represented is 4-amino-butyraldehyde-diacetal.

Example 1

Synthesis of an Aldehyde Derivative of HA Having an Average Molecular Weight of 200 kDa 5.00 g of hyaluronic acid of a sodium salt fermentative origin hyalastine fraction (MW 200 kDa) are dissolved in 250 ml of water and the resulting solution is percolated through a glass column pre-filled with 100 $cm^3$ of Dowex resin in the form of tetrabutylammonium. The eluted HA salt solution of TBA is collected and freeze-dried. 7.50 g of product are obtained, which are dissolved in 400 ml of N-methyl-pyrrolidone (NMP).

After the complete dissolution of the HA salt, 300 mg of carbonyl-diimidazole (CDI), 450 µl of methanesulfonic acid and 387 mg of 4-aminobutyraldehyde diethylacetal are added and the mixture is left to react at 40° C. overnight under gentle stirring. The reaction is stopped by adding 0.1 volumes of a saturated aqueous solution of NaCl and, after 30 minutes, the solution is added to 3 volumes of absolute ethanol to separate the HA derivative according to FIG. 1 from the reaction mixture.

Figure 2:
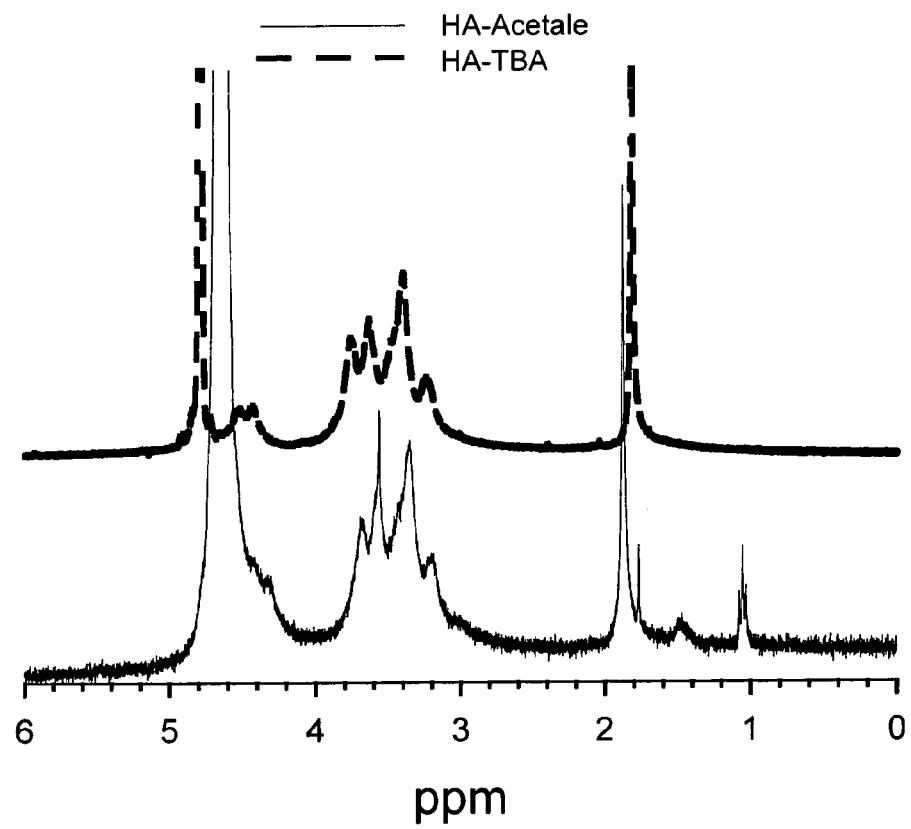

The precipitate is washed again in ethanol and finally dried in a high vacuum at 40° C. 4.49 g of derivative are obtained, containing 13% in moles of protected aldehyde groups with respect to the repetitive units of HA. The NMR spectrum of this product, whose synthesis has been effected as indicated herein, is shown in FIG. 2.

Example 2

Synthesis of an Aldehyde Derivative of HA Having an Average Molecular Weight of 100 kDa 4.00 g of the sodium salt of hyaluronic acid having an average molecular weight of 100 kDa, of an extractive origin, are dissolved in 500 ml of water for injectable preparations. The solution obtained is brought to a temperature of 4° C. and 290 mg (15% in moles) of EDC, 175 mg of NHS and 245 mg of 4-aminobutyraldehyde diethylacetal are then added. After 18 hours of reaction, the product is precipitated by the addition of 4 volumes of absolute ethanol and washed with hydroalcohol mixtures with an increasing content of ethanol until reaching absolute ethanol. The product proves to be substituted at 11.9% moles/moles.

Example 3

Synthesis of an HA-Interferon Conjugate 3.00 g of the aldehyde derivative of HA (activated intermediate) according to Example 1 are dissolved at a concentration of 10 mg/ml in an acid environment by the presence of phosphoric acid at a temperature of 60° C. for 2 hours. $4 \times 10^{-5}$ moles of recombinant human interferon alpha 2a, $4 \times 10^{-4}$ moles of cyanoborohydride are added to the hydrolyzed product previously cooled and the pH is regulated to 6.0. After 24 h of reaction, the adduct is purified by dialysis against water and then freeze-dried. The purity is verified by dimensional exclusion chromatography (GPC), with the corresponding chromatogram illustrated in FIG. 5.

Figure 5:
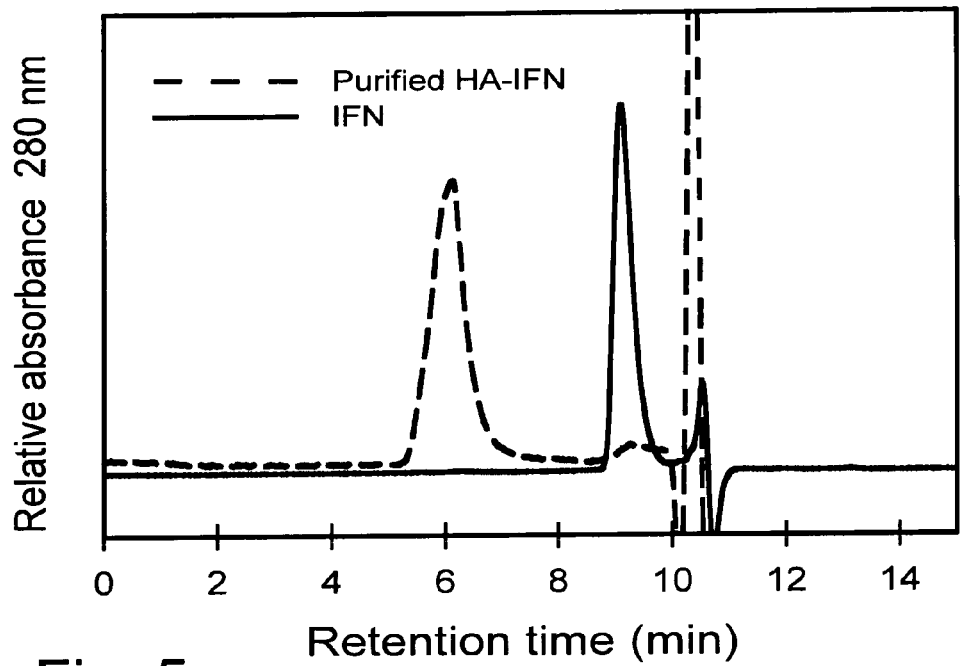
FIG. 5 shows the chromatogram of the HA-IFN conjugate which respectively shows free and conjugated IFN.

The bioconjugate HA-IFN was subjected to SDS-PAGE Western Blot, with human anti-IFN alpha antibodies. A presence of free protein lower than 5% was revealed by means of densitometric techniques. This result is coherent with what emerged from the dimensional exclusion chromatography (FIG. 5).

Example 4

Determination In Vitro of the Biological Activity of the HA-IFN Conjugate

The determination of the biological activity of the HA-IFN conjugate was effected by means of a method prepared ad hoc.

The experiments were carried out on a human primary cell line of ovarian carcinoma (pdOVCA1), sensitive to the antiproliferative action of IFN. The cells were seeded at a concentration of 10,000 cells/well and incubated alone and in the presence of:

HA-IFN bioconjugate prepared as in Example 3 at a concentration of 1,000, 500, 250 U/ml as equivalent IFN Unit;
Recombinant human Interferon alpha 2a at a concentration of 1,000, 500, 250 U/ml;
HA having a molecular weight of 200 kDa, i.e. the same used for preparing the conjugate, at a concentration of 323.5, 162.75, 81.375 µg/ml.

Figure 4:
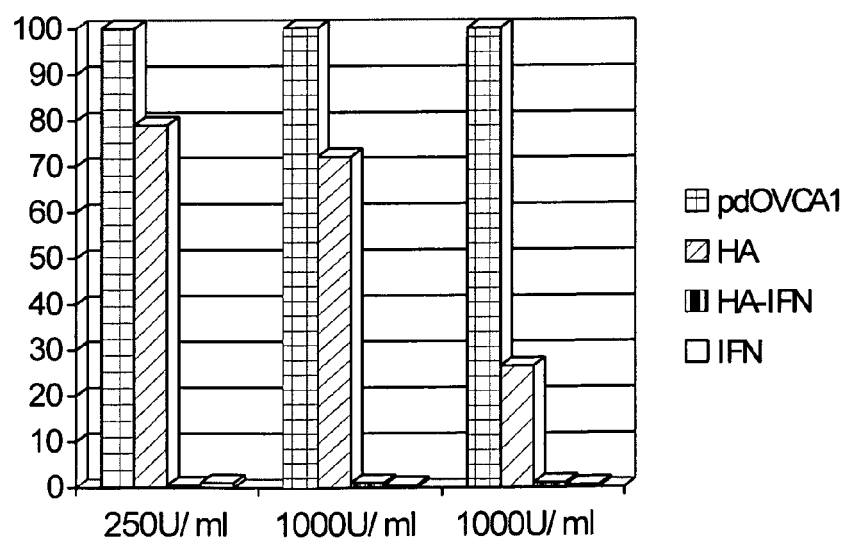
FIG. 4 shows the results of the cytotoxicity test (ATPlite) in HA-IFN conducted on a human primary cell line of ovarian carcinoma (pdOVCA1), sensitive to the antiproliferative action of the IFN.

After 5 days of incubation, the cell vitality was measured via the ATPlite cytotoxicity test. The results obtained are summarized in FIG. 4, where the cell vitality is expressed in percentage with respect to the level obtained for the cells incubated alone.

As can be seen, the recombinant human Interferon alpha 2a exerts a marked cytotoxic action with respect to this cell line. This property is almost quantitatively maintained in the conjugate, whereas the non-conjugated HA is not capable of exerting this action.

Example 5

Determination In Vivo of the Biological Activity of the Conjugate HA-IFN

The experiments were carried out using the cell line of ovarian carcinoma (pdOVCA1) (sensitive to the antiproliferative action of IFN) inoculated i.p. in mice belonging to the group SCID F, $3 \times 10^6$ cells/mouse. The experiment was effected using 3 distinct groups of animals, 6 mice per group:

$1^{st}$ group: treatment at the $7^{th}$, $14^{th}$ and $21^{st}$ day with recombinant human Interferone alpha 2a (IFN) at a concentration of 1,000 U/ml, as positive control;
$2^{nd}$ group: treatment at the $7^{th}$, $14^{th}$ and $21^{st}$ day with the bioconjugate object of the present invention (HA-IFN) prepared as described in Example 3, at a concentration of 1,000 U/ml as equivalent IFN unit;
$3^{rd}$ group; represents the non-pharmacologically treated control but only inoculated with pdOVCA1s.

Figure 10:
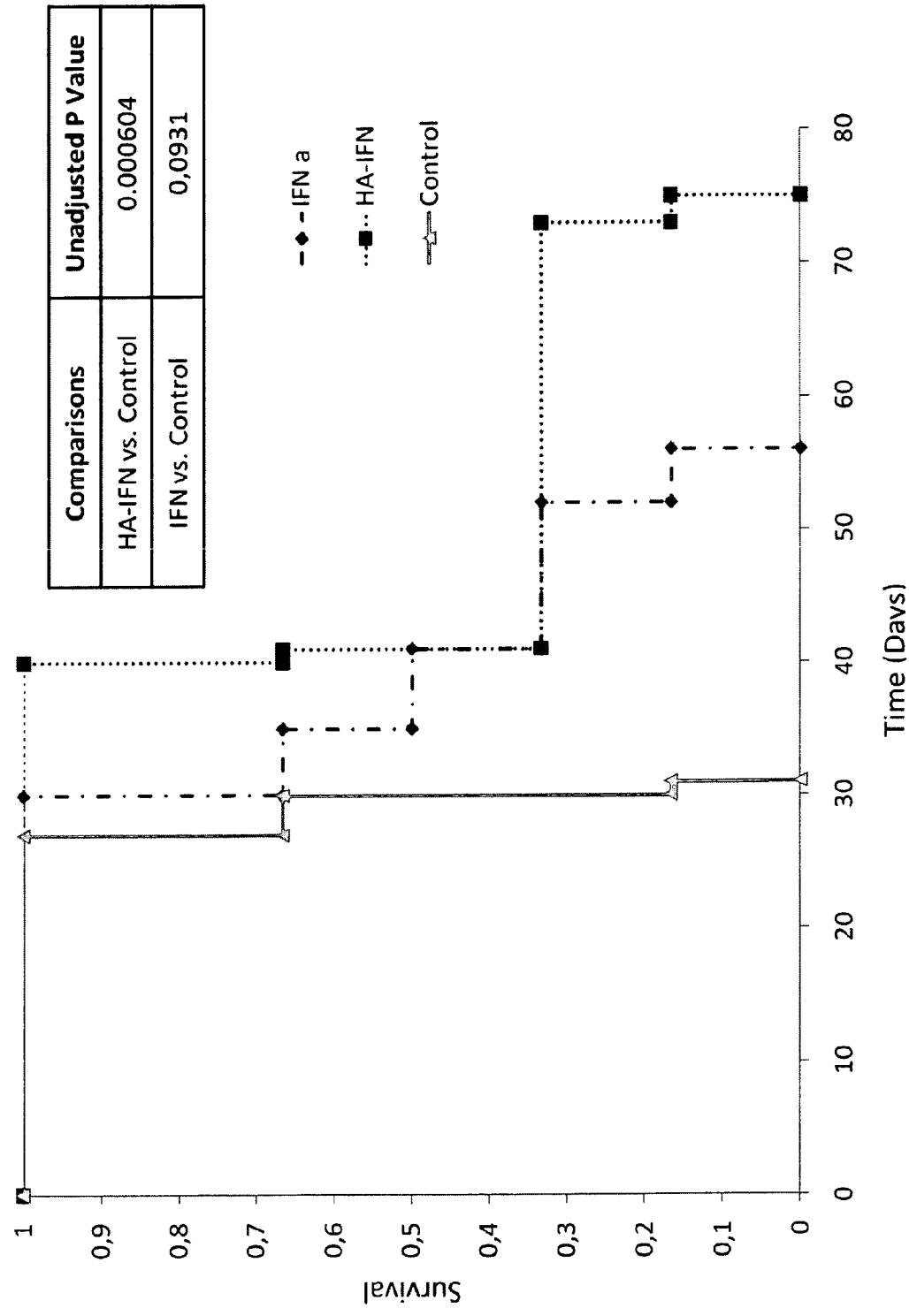
FIG. 10 shows the efficacy in vivo of the bioconjugate HA-IFN vs IFN vs the non-treated product.

The results are summarized in FIG. 10; the above experimentation clearly shows the greater efficacy in vivo of the bioconjugate HA-IFN vs the reference drug IFN. As a further confirmation of the result, the statistic evaluations indicate the considerable significance of the bioconjugate vs the non-treated control, whereas no statistic significance is revealed of the result obtained from the positive control vs the non-treated product.

Example 6

Synthesis of an HA-Interferon Conjugate Marked with a Fluorescent Probe

Care being taken to effect every passage under sterility conditions, 12.5 mg of recombinant human Interferon alpha 2a are marked with 0.5 mg of Cy5 according to the instructions received from the supplier (GE Healthcare). A coupling reaction is effected with the marked protein, purified by exhaustive dialysis against water, according to the instructions provided in Example 3. 90.4 mg of product are obtained.

Example 7

Figure 3:
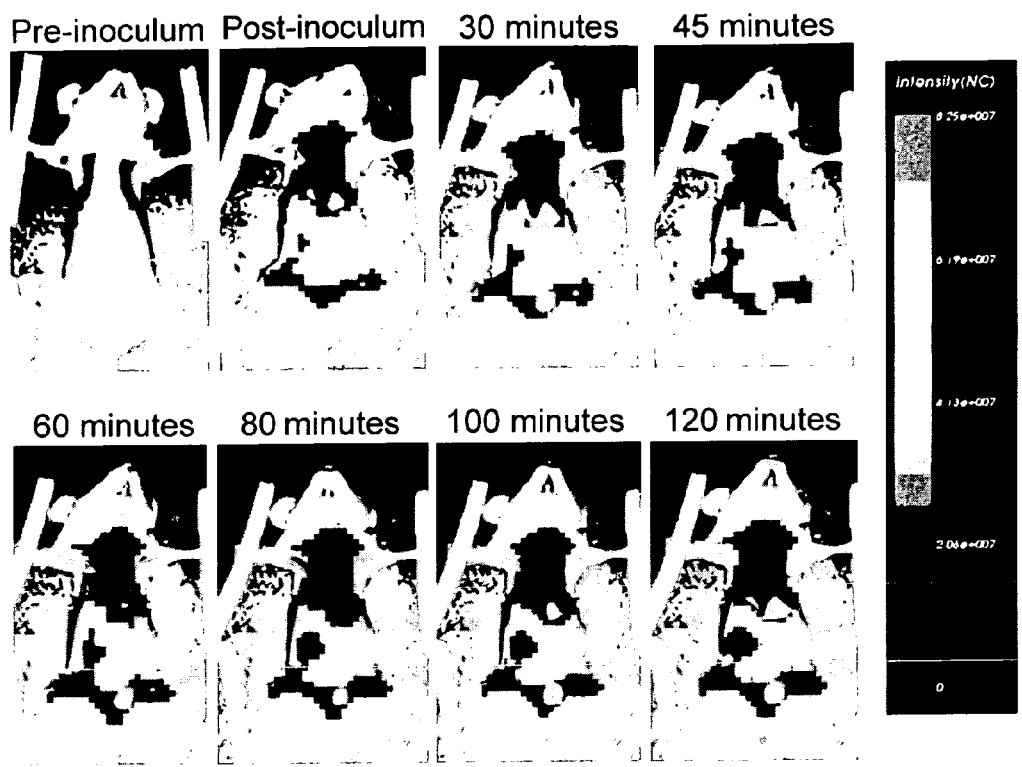
FIG. 3 shows fluorescence tomographic images after endovenous administration of the HA-IFN conjugate marked with a fluorescent probe in mice.

Biodistribution In Vivo by Fluorescence Tomography of the HA-Interferon Conjugate Marked with a Fluorescent Probe The biodistribution of the conjugate after endovenous administration was determined in vivo through a preclinical optical imaging system Explore Optix (GE Healthcare). The system consists in an apparatus for measuring the bioluminescence which is adapted for tomographically reconstructing whole body images of small rodents. The technology used is "time correlated single photon counting", to measure absorption and fluorescence with its lifetime) of fluorescent probes, allowing their three-dimensional localization. The images shown in FIG. 3 represent the result of the inoculation experiment in the anaesthetized mouse of the labeled conjugate according to Example 6. Before inoculation no signal can be found. Immediately after inoculation, a hepatic accumulation is observed, associated with a less intense fluorescence in the adjacent pulmonary area, which is prevalently caused by a non-specific entrapment in the pulmonary microcirculation. An accumulation in the pelvic region is associated with these signals, which in a longer time scale leads to a vesical accumulation.

Example 8

Synthesis of an HA-hGH Conjugate 1.00 g of the aldehyde derivative of HA according to Example 1 are dissolved at a concentration of 10 mg/ml in an acid environment by the presence of phosphoric acid at a temperature of 60° C. for 2 hours. $2 \times 10^{-5}$ moles of recombinant human growth hormone, $2 \times 10^{-1}$ moles of cyanoborohydride are added to the hydrolyzed product previously cooled and the pH is regulated to 6.0. After 24 h of reaction, the adduct is purified by dialysis against water and then freeze-dried.

Example 9

Figure 7:
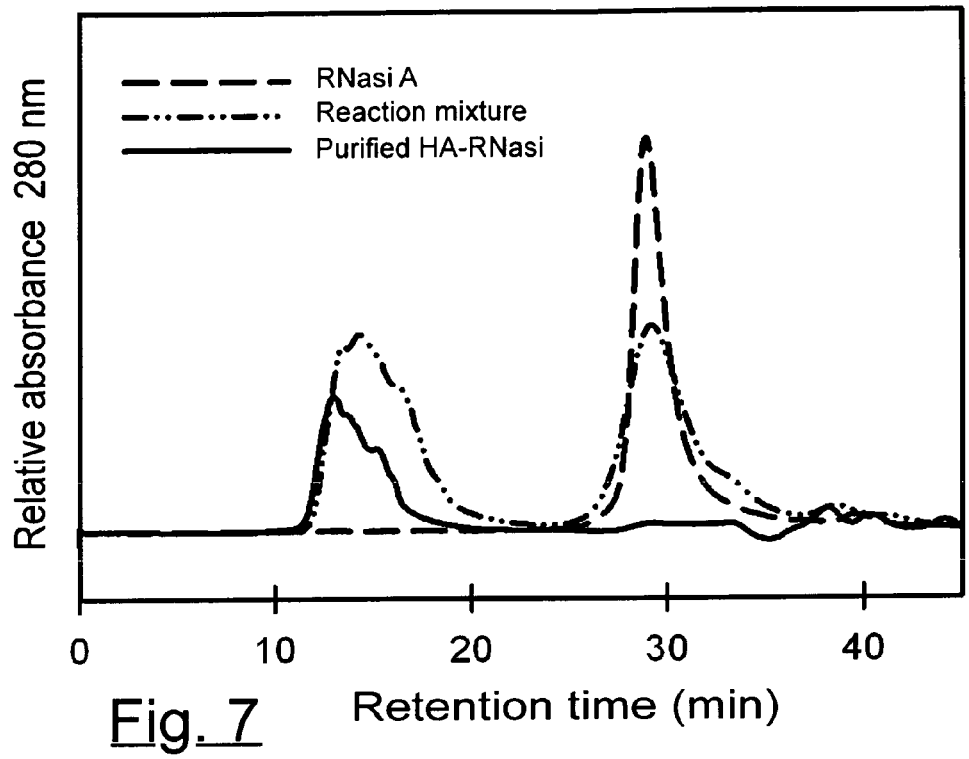
FIG. 7 shows the chromatogram of the HA-RNAse conjugate which respectively shows free and conjugated RNAsI enzyme.

Synthesis of an HA-RNAsi A Conjugate 1.00 g of the aldehyde derivative of HA according to Example 1 are dissolved at a concentration of 8 mg/ml in an acid environment by the presence of phosphoric acid at a temperature of 50° C. for 2 hours. The pH is regulated to 6.0 and $2 \times 10^{-5}$ moles of RNAse A and $2 \times 10^{-1}$ moles of cyanoborohydride are added to the hydrolyzed product previously cooled. At this pH the reaction takes place specifically at the N-terminal end of the protein. After 24 h of reaction, the adduct is purified by dialysis against water and then freeze-dried. The corresponding GPC chromatogram registered under the conditions described in Example 14 can be found in FIG. 7. This type of conjugate is optimally suitable for measuring in vitro the residual activity of the enzyme, using a specific kit based on the evaluation of the absorption increase at 287 nm with time, determined by hydrolysis of the specific synthetic substrate cyclic 2',3'-cytidine monophosphate (2', 3'-CMC).

A comparison of the residual activity of the enzyme, free or bound to HA, produces the following results:

| PRODUCT | % Relative enzymatic activity |
|---|---|
| RNAsi A | 100 |
| HA-Ac-RNAsi A | 95.23 |

The quantitative maintenance of the enzymatic activity shows that the conjugation reaction in no way degrades the protein.

Example 10

Figure 8:
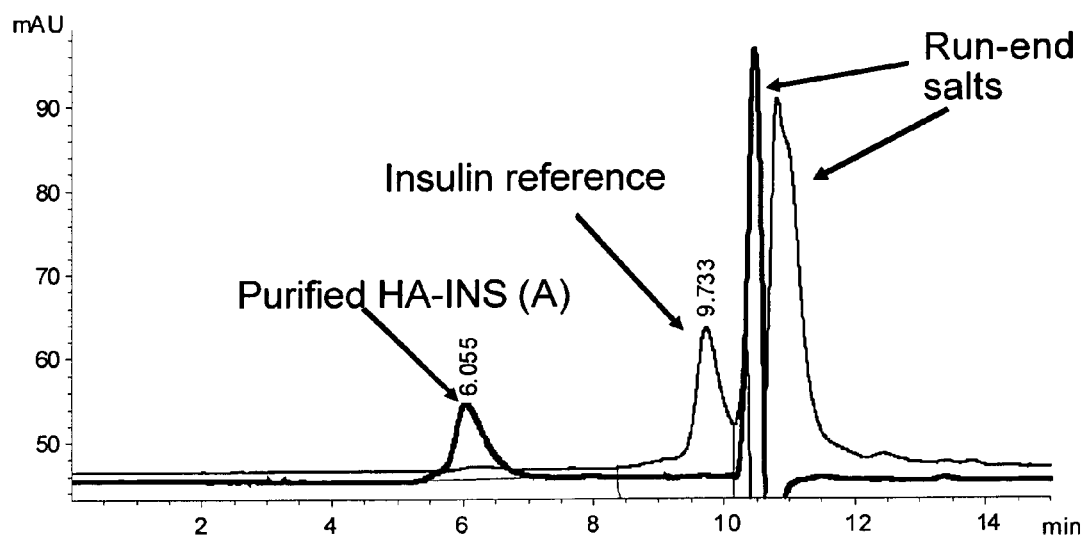
FIG. 8 shows the chromatogram of the HA-insulin conjugate which respectively shows free and conjugated insulin.

Synthesis and Activity In Vivo of the HA-Insulin Conjugate 3.00 g of the aldehyde derivative of HA (activated intermediate) according to Example 1 are dissolved at a concentration of 10 mg/ml in an acid environment by the presence of phosphoric acid at a temperature of 60° C. for 2 hours. $4 \times 10^{-5}$ moles of insulin, $4 \times 10^{-1}$ moles of cyanoborohydride are added to the hydrolyzed product previously cooled and the pH is regulated to 6.0. After 24 h of reaction, the adduct is purified and analyzed via dimensional exclusion chromatography; the relative chromatogram is visible in FIG. 8. The activity in vivo of the conjugate is evaluated on a model of induced diabetes type I in a rat after administration of streptozocin at a dose of 70 mg/Kg.

Figure 9:
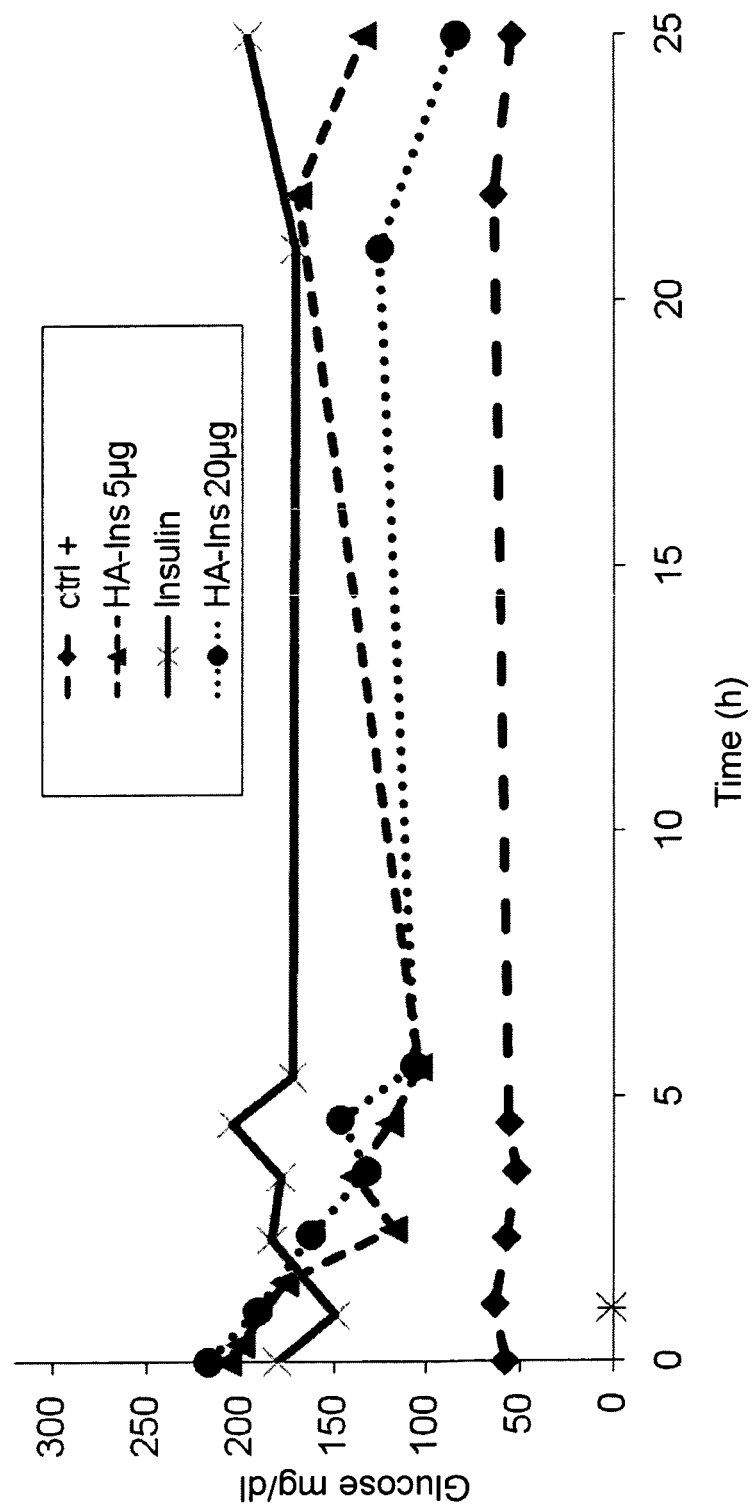
FIG. 9 shows the biological activity in vivo of the HA-Insulin conjugate administered subcutaneously at a dose of 5 μg or 20 μg of insulin by the determination of the glucose levels in the blood of animals treated with respect to the control and non-treated animals.

The HA-Insulin conjugate is administered subcutaneously at a dose of 5 or 20 μg of equivalent insulin. The biological activity of the conjugate is tested through the determination of the glucose levels in the blood of animals, measured by means of commercial kits (OneTouch® II, LifeScan, Johnson & Johnson), The control consists of healthy rats (group 1) and rats with induced diabetes treated with insulin (group 2). The results are illustrated in FIG. 9.

The rats treated with insulin belonging to group 2 show a sudden decrease in the glucose level in the blood, which however returns to high values in a relatively rapid time scale. The HA-Insulin conjugate has an effect which is exerted more slowly, but has a considerably prolonged duration with time, bringing the concentration of glucose, within a time span of 5 hours, to a lower level than the group treated with insulin alone, and maintaining this effect for the 24 hour duration of the experiment.

These results demonstrate that the bioconjugate according to the invention is capable of doubling the effectiveness of the conjugated drug (in this specific case insulin) maintaining it with time.

The test therefore shows that the bioconjugates according to the present invention or biomaterials prepared from these, are suitable for producing systems for the prolonged release of therapeutic agents, including therapeutic proteins, due to their capacity of increasing the therapeutic effectiveness, maintaining it with time.

Example 11

Synthesis and Determination of the Biological Activity of the Conjugate HA-Calcitonin (HA-sCT)

10 mg of HA-acetal are dissolved at a concentration of 10 mg/ml in phosphoric acid 10 mM, pH 2.1 at a temperature of 60° C. for 1 hour. After regulating the pH to 6.0 with NaOH 0.1 N and leaving the solution to cool to room temperature, $1.25 \times 10^{-3}$ mmoles of salmon calcitonin (sCT) are added to the hydrolyzed product and after 30 minutes $5.8 \times 10^{-2}$ mmoles of sodium cyanoborohydride. After 48 h of reaction, the adduct is purified and analyzed by dialysis against water (2 L) for 24 hours using a membrane with a cut-off of 50 kDa. After dialysis, the product is freeze-dried, the concentration of protein is determined by bicinchoninic acid assay (BCA; Sigma Aldrich) and absorption at 280 nm.

The purity of the conjugate is verified by means of gel-filtration chromatography (GPC), the corresponding chromatogram is shown in FIG. 11.

The loading of calcitonin in the conjugate is 9.1% (w/w).

The activity in vivo of the conjugated calcitonin (HA-sCT) was evaluated following the hypocalcemic effect measured after endovenous administration in rats.

The experiments were carried out on Sprangue-Dawley rats having a weight of 180-250 g. The rats were divided into 4 groups with 3 animals in each group and different preparations were administered to each group: sCT, HA-sCT, HA and saline solution. sCT and HA-sCT and HA were dissolved in a physiological solution and filtered with an 0.22 μm filter. The calcitonin and conjugate were administered at a dosage of 40

μg/kg (calcitonin equiv.). HA was administered as control in the same quantities present in the conjugate. After administration through the caudal vein, blood samples were taken at pre-established times (0, 0.5, 1, 2, 3, 4, 5, 6, 24 hours) and preserved in a refrigerator until the moment of use. After centrifugation for 20 minutes at 1,000×g, the plasma was collected and the presence of calcium in the plasma was evaluated by means of colorimetric assay (Colorimetric Calcium Assay kit, Vinci-Biochem).

The results obtained are summarized in FIG. 12, where the percentage variation of calcium in the plasma is expressed with time. The sCT has its maximum effect an hour after administration and, after 6 hours, the calcium levels rise again towards the basic values. The conjugate, on the contrary, shows a more prolonged hypocalcemizing action and a more marked effect. The HA and saline solution do not cause any variations in the calcium in the blood.

Example 12

Synthesis of an BA-IL1-ra Conjugate 10 mg of HA-acetal are dissolved at a concentration of 10 mg/ml in phosphoric acid 10 mM, pH 2.1 at a temperature of 60° C. for 1 hour. After regulating the pH to 6.0 with NaOH, 0.1 N and leaving the solution to cool to room temperature, $2.46 \times 10^{-4}$ mmoles of IL-1-ra are added to the hydrolyzed product and after 30 minutes $1.16 \times 10^{-2}$ mmoles of sodium cyanoborohydride. After 48 h of reaction, the adduct is purified by dialysis against a phosphate buffer 0.1 M, pH 6.5 (2 L) for 24 hours using a membrane with a cut-off of 50 kDa. After dialysis, the concentration of protein is determined by colorimetric assay (BCA assay; Sigma Aldrich). The conjugate is maintained in solution at 4° C. The purity is verified by means of gel-filtration chromatography (GPC), the corresponding chromatogram is shown in FIG. 13.

Example 13

Synthesis of an HA-Lubricin Conjugate 10 mg of HA-acetal are dissolved at a concentration of 10 mg/ml in phosphoric acid 10 mM, pH 2.1 at a temperature of 60° C. for 1 hour. After regulating the pH to 6.0 with NaOH, 0.1 N and leaving the solution to cool to room temperature, $2.50 \times 10^{-4}$ moles of Lubricin are added to the hydrolyzed product and after 30 minutes $1.16 \times 10^{-2}$ moles of sodium cyanoborohydride. After 48 h of reaction, the adduct is purified by dialysis against a phosphate buffer 0.1 M pH 6.5 (2 L) for 24 hours using a membrane with a cut-off of 50 kDa. After dialysis, the concentration of protein is determined by colorimetric assay (BCA assay; Sigma Aldrich). The conjugate is maintained in solution at 4° C. The purity is verified by means of gel-filtration chromatography (GPC).

Example 14

Characterization via GPC of the Synthesized Conjugates

In order to determine the presence of free protein in the synthesized conjugates, the preparations according to Examples 3, 8, 9 and 10 were subjected to high-pressure dimensional exclusion chromatography. For the conjugate HA-IFN according to Example 3 and HA-Insulin according to Example 10, the chromatogram (FIG. 5 and FIG. 8) was registered on an Agilent GF-250 column with an eluent consisting of a phosphate buffer 0.2M at pH=7.0+NaCl $10^{-1}$ M 80%+Acetonitrile 20%, with a flow of 0.3 ml/min.

Figure 6:
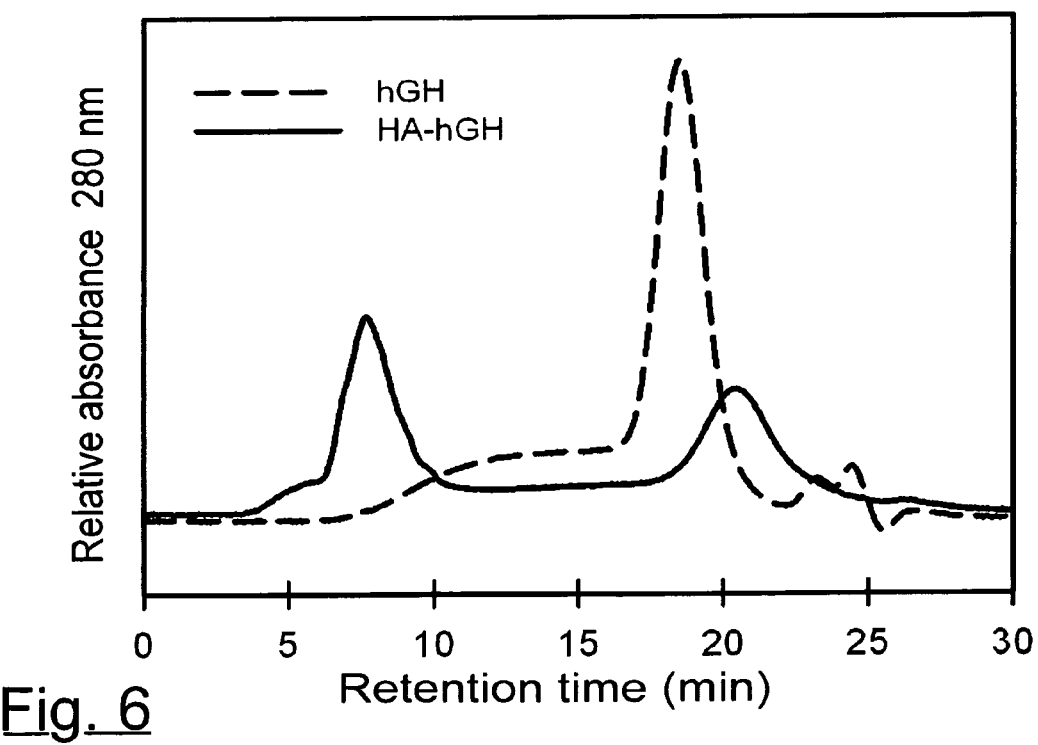
FIG. 6 shows the chromatogram of the HA-hGH conjugate which respectively shows free and conjugated hGH.

The chromatograms relating to the other conjugates (FIG. 6, FIG. 7) were registered with a Superose 12 column, UV detection at 280 nm, with an eluent consisting of a phosphate buffer $10^{-1}$ M a pH=7.2+NaCl 0.2M 80%+Acetonitrile 20%, with a flow of 0.8 ml/min.

Example 15

Synthesis of the Aldehyde Derivative of Condroitin Sulfate as Activated Intermediate 5.00 g of condroitin sulfate of an extractive origin (with the sulfate group prevalently in position 4 of the N-acetyl galactosamine unit) are dissolved in 250 ml of water and the resulting solution is percolated through a glass column pre-filled with 100 cm$^3$ of Dowex resin in the form of tetrabutylammonium. The eluted TBA salt solution of condroitin sulfate is collected and freeze-dried. 7.75 g of product are obtained, which are dissolved in 400 ml of N-methyl-pyrrolidone (NMP).

After the complete dissolution, 345 mg of carbonyl-diimidazole (CDI), 460 μl of methanesulfonic acid and 396 mg of 4-aminobutyraldehyde diethylacetal are added and the mixture is left to react at 45° C. overnight under light stirring.

The derivatization process is stopped by adding 0.1 volumes of a saturated aqueous solution of NaCl. The reaction mixture is dialyzed against a saline solution by NaCl 0.9% then against pure water, and freeze-dried. 4.13 g of a light brown-coloured granular solid are obtained.

The invention claimed is:

1. A process for the synthesis of a conjugate of a glycosaminoglycan (GAG) with a biologically active molecule, comprising:
    a) derivatizing a GAG with at least one aldehyde group (CHO), by producing an adduct by reacting said GAG with a spacer molecule (SP) to bind said GAG to said SP via an amide bond, wherein said spacer molecule comprises (i) one or more aldehyde groups (SP-CHO), said aldehyde groups (SP-CHO) being optionally protected and (ii) a nucleophilic group suitable for conjugation with said GAG; wherein
    when said one or more aldehyde group(s) is protected, said SP-CHO groups are hydrolyzed with an aqueous acid;
    b) reacting the adduct obtained in step a) with at least one biologically active molecule (TA) which comprises a functional group capable of reacting with the aldehyde group, wherein said TA is a member selected from the group consisting of polypeptides, proteins, nucleic acids and therapeutic agents containing at least one amine group not fundamental for biological functioning.

2. The process according to claim 1, wherein said optionally protected SP-CHO group are prepared by reacting said aldehydes with an aliphatic or aryl aliphatic alcohol or diol selected from the group consisting of methanol, ethanol, n-propanol, isopropanol, n-butanol, sec-butanol, tert-butanol, iso-butanol, ethylene glycol, propylene glycol, 1,3-propandiol, 1,4-butandiol to form isolable acetals.

3. The process according to claim 1, wherein said spacer molecule SP-(CHO) is an amino aldehyde.

4. The process according to claim 1, wherein said hydrolysis takes place at a pH ranging from 1.5 to 3.0, at a temperature ranging from 25 to 65° C., for at least 30 minutes.

5. The process according to claim 1, wherein said nucleophilic group is an amine group, in a free or salified form, or an alcohol group.

6. The process according to claim 1, wherein said functional group of the biologically active molecule capable of reacting with aldehydes, is an amine group which can be naturally present or introduced by synthesis.

7. The process according to claim 1, wherein said GAG is a member selected from the group consisting of hyaluronic acid (HA), condroitin sulfate, dermatan sulfate, keratan sulfate, heparin, heparan sulfate or derivatives thereof.

8. The process according to claim 1, wherein said biologically active molecule is a polypeptide or a protein selected from the group consisting of:
Immunomodulators;
Growth factors;
Cytokiness;
Glycoproteins;
Enzymes;
Antibodies;
Hormones.

9. The process according to claim 1, wherein when said biologically active molecule is a member selected from the group consisting of:
Antitumoral drugs;
Antiviral agents and antibiotics;
Protease and polymerase inhibitors;
Anti-inflammatory, analgesic, anesthetic, anti-pain drugs;
Narcotics;
Steroids; and
Minoxidyl.

10. The process according to claim 1, wherein said biologically active molecule is a nucleic acid selected from the group consisting of: small interfering RNA, MicroRNAs, and antisense RNA.

11. The process according to claim 1, comprising:
a) derivatizing hyaluronic acid (HA), or a HA salt soluble in an aprotic organic polar solvent, with at least one aldehyde group (CHO), through the reaction of HA with protected amino-aldehydes effected in an aqueous medium in 1-Ethyl-3-(3-dimethylaminopropyl)carbodiimide (EDC)+(NHS) to form an amide or in an aprotic solvent; and hydrolyzing the obtained intermediate in order to release the aldehyde group, in phosphoric acid at a pH ranging from 1.5 to 3.0, at a temperature ranging from 25 to 65° C., for at least 30 minutes;
b) reacting the product obtained in step a) with said biologically active molecule.

12. The process according to claim 11, wherein said HA is selected from hyaluronic acid salified with organic and/or inorganic bases; esters of hyaluronic acid with alcohols of the aliphatic, aryl aliphatic, cyclo aliphatic, aromatic, cyclic and heterocyclic series with an esterification percentage ranging from 20 to 80%; amides of HA with amines of the aliphatic, aryl aliphatic, cyclo aliphatic, aromatic, cyclic and heterocyclic series, with an amidation percentage ranging from 0.1 to 50%; O-sulfated derivatives of hyaluronic acid up to the fourth sulfation degree; internal esters of hyaluronic acid with an esterification percentage lower than 20%; deacetylated compounds of hyaluronic acid with a deacetylation percentage of 0.1 to 30%; and percarboxylated derivatives of hyaluronic acid with a percarboxylation degree of 0.1 to 100%.

13. The process according to claim 11, wherein said biologically active molecule is a protein or polypeptide and said functional group is an amine group.

14. The process according to claim 13, wherein said protein or polypeptide is added to the intermediate product obtained in step a) under reducing conditions with sodiumcyanoborohydride or lithium aluminum hydride or sodium borohydride.

15. The process according to claim 11, wherein said polypeptide or protein is selected from the group consisting of interferons, erythropoietins, haematopoiesis stimulating factors, bone/cartilage growth factors, growth hormone, lubricin, insulin, calcitonin, and IL1-ra.

16. The process according to claim 11, wherein said salt of HA is a tetrabutyl ammonium salt of HA (HATBA).

17. The process according to claim 3, wherein said spacer molecule comprises an acetal protecting group.

18. The process according to claim 4, wherein said pH is in the range of 2.0 to 2.5 and said temperature ranges from 40 to 60° C.

19. The process according to claim 7, wherein said salts are salts with sodium, potassium, magnesium, calcium, or quaternary ammonium salts.

20. The process according to claim 7, wherein said derivatives comprise carboxylic esters, o-esters, amides, percarboxylated derivatives, O-sulfated derivatives, N-deacylated derivatives and N-sulfated derivatives.

21. The process according to claim 8, wherein
said immunomodulator is a member selected from the group consisting of Interferons of type I, Interferons of type II and Interferons of type III;
said growth factor is a member selected from the group consisting of Erythropoietins, ESA molecules, Erythropoiesis stimulating factors, such as GM-CSF and G-CSF factors, and Growth factors for the bones and cartilages;
said cytokine is a member selected from the group consisting of IL2, TNF and their receptor antagonists with their soluble receptors, IL1-ra, and the soluble receptors of pro-inflammatory cytokines;
said Glycoprotein protein is Lubricin;
said enzyme is a member selected from the group consisting of superoxide dismutases, RNAse and glucocerebrosidase;
said hormone is a member selected from the group consisting of Calcitonin, Insulin and its analogues, and the growth hormone.

22. The process according to claim 9, wherein said biologically active molecule is a member selected from the group consisting of taxanes, Vinca alkaloids, camptothecins, substituted ureas; complexes of platinum, gold, silver or other metals; methotrexate, trimetrexate, pemetrexed, tetrahydrofolate; analogues of pyrimidine, cytidine, purine; oncological antibiotics and anthracenediones.

23. The process according to claim 8, wherein said hormone is calcitonin.

24. A process for the synthesis of a conjugate of a glycosaminoglycan (GAG) with a biologically active molecule, comprising:
a) derivatizing a GAG with at least one aldehyde group (CHO), by producing an adduct by reacting said GAG with a spacer molecule (SP) that is an amino aldehyde to bind said GAG to said SP via an amide bond, wherein said spacer molecule comprises (i) one or more aldehyde groups (SP-CHO), said aldehyde groups (SP-CHO) being optionally protected and (ii) a nucleophilic group suitable for conjugation with said GAG, said nucleophilic group being an amine or alcohol group; wherein when said one or more aldehyde group(s) is protected, said SP-CHO groups are hydrolyzed with an aqueous acid, wherein said hydrolysis takes place at a pH ranging from 1.5 to 3.0, at a temperature ranging from 25 to 65° C., for at least 30 minutes;

b) reacting the adduct obtained in step a) with at least one biologically active molecule (TA) which comprises a functional group capable of reacting with the aldehyde group, wherein said TA is a member selected from the group consisting of polypeptides, proteins, nucleic acids and therapeutic agents containing at least one amine group not fundamental for biological functioning, wherein said optionally protected SP-CHO group are prepared by reacting said aldehydes with an aliphatic or aryl aliphatic alcohol or diol selected from the group consisting of methanol, ethanol, n-propanol, isopropanol, n-butanol, sec-butanol, tert-butanol, iso-butanol, ethylene glycol, propylene glycol, 1,3-propandiol, 1,4-butandiol to form isolable acetals.

25. The process according to claim 24, wherein said GAG is a member selected from the group consisting of hyaluronic acid (HA), condroitin sulfate, dermatan sulfate, keratan sulfate, heparin, heparan sulfate or derivatives thereof.

26. The process according to claim 24, wherein said biologically active molecule is a polypeptide or a protein selected from the group consisting of:

Immunomodulators;
Growth factors;
Cytokiness;
Glycoproteins;
Enzymes;
Antibodies;
Hormones.

27. The process according to claim 24, wherein when said biologically active molecule is a member selected from the group consisting of:

Antitumoral drugs;
Antiviral agents and antibiotics;
Protease and polymerase inhibitors;
Anti-inflammatory, analgesic, anesthetic, anti-pain drugs;
Narcotics;
Steroids; and
Minoxidyl.

28. The process according to claim 24, wherein said biologically active molecule is a nucleic acid selected from the group consisting of: small interfering RNA, MicroRNAs, and antisense RNA.

* * * * *